United States Patent [19]
Delaplane et al.

[11] Patent Number: 5,975,080
[45] Date of Patent: Nov. 2, 1999

[54] RETENTION SYSTEM FOR ANTI-DISCONNECT APPARATUS AND METHOD, FOR BREATHING SYSTEMS

[75] Inventors: David Delaplane; Robert Bohning, both of Simi Valley, Calif.

[73] Assignee: Hammer-Plane, Inc., Simi Valley, Calif.

[21] Appl. No.: 09/010,883

[22] Filed: Jan. 22, 1998

[51] Int. Cl.$^6$ ................................................. A61M 16/00
[52] U.S. Cl. .............................. 128/207.17; 128/207.15
[58] Field of Search ..................... 128/207.17, 207.15, 128/200.24, 207.14, 202.27

[56] References Cited

U.S. PATENT DOCUMENTS

| | | |
|---|---|---|
| 1,592,345 | 7/1926 | Drager . |
| 1,835,757 | 12/1931 | Burchett . |
| 2,765,792 | 10/1956 | Nichols . |
| 2,928,387 | 3/1960 | Layne . |
| 3,039,469 | 6/1962 | Fountain . |
| 3,086,529 | 4/1963 | Munz et al. . |
| 3,236,236 | 2/1966 | Hudson . |
| 3,535,719 | 10/1970 | Murcott . |
| 3,688,774 | 9/1972 | Akiyama . |
| 3,927,676 | 12/1975 | Schultz . |
| 3,946,742 | 3/1976 | Eross . |
| 3,973,569 | 8/1976 | Sheridan et al. . |
| 3,987,798 | 10/1976 | McGinnis . |
| 4,018,221 | 4/1977 | Rennie . |
| 4,027,666 | 6/1977 | Marx . |
| 4,088,136 | 5/1978 | Hasslinger et al. . |
| 4,235,229 | 11/1980 | Ranford et al. . |
| 4,246,897 | 1/1981 | Muto . |
| 4,256,099 | 3/1981 | Dryden . |
| 4,304,228 | 12/1981 | Depel . |
| 4,313,437 | 2/1982 | Martin . |
| 4,331,144 | 5/1982 | Wapner . |
| 4,485,822 | 12/1984 | O'Connor et al. . |
| 4,527,559 | 7/1985 | Roxburg et al. . |
| 4,548,200 | 10/1985 | Wapner . |
| 4,598,705 | 7/1986 | Lichtenberger . |
| 4,641,646 | 2/1987 | Schultz et al. . |
| 4,738,662 | 4/1988 | Kalt et al. . |
| 4,838,867 | 6/1989 | Kalt et al. . |
| 4,844,061 | 7/1989 | Carroll . |
| 4,848,331 | 7/1989 | Northway-Meyer . |
| 4,906,234 | 3/1990 | Voychehovski . |
| 5,009,227 | 4/1991 | Nieuwstad . |
| 5,042,477 | 8/1991 | Lewis . |
| 5,054,482 | 10/1991 | Bales . |
| 5,056,515 | 10/1991 | Abel . |
| 5,069,206 | 12/1991 | Crosbie . |
| 5,101,822 | 4/1992 | Kimmel . |
| 5,123,410 | 6/1992 | Green et al. . |
| 5,282,463 | 2/1994 | Hammersley ...................... 128/207.15 |
| 5,357,952 | 10/1994 | Schuster et al. . |
| 5,471,980 | 12/1995 | Varner . |

*Primary Examiner*—John G. Weiss
*Assistant Examiner*—Charles W. Anderson
*Attorney, Agent, or Firm*—William W. Haefliger

[57] ABSTRACT

The method of connecting flexible first band structure to a tracheostomy neck plate, the neck plate having a first wing projecting laterally, the includes providing first clip structure configured to embrace the wing, the band structure attached to the clip structure; displacing the clip structure relative to the wing, to embrace the wing; and providing a detent connection on at least one of the clip structure and wing to releasably interconnect the clip structure and wing in response to said relative displacing of the clip structure to embrace the wing.

13 Claims, 5 Drawing Sheets

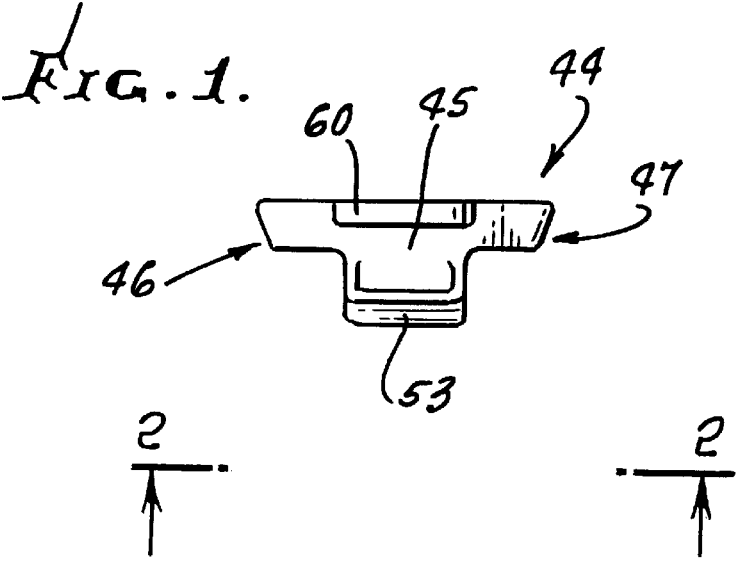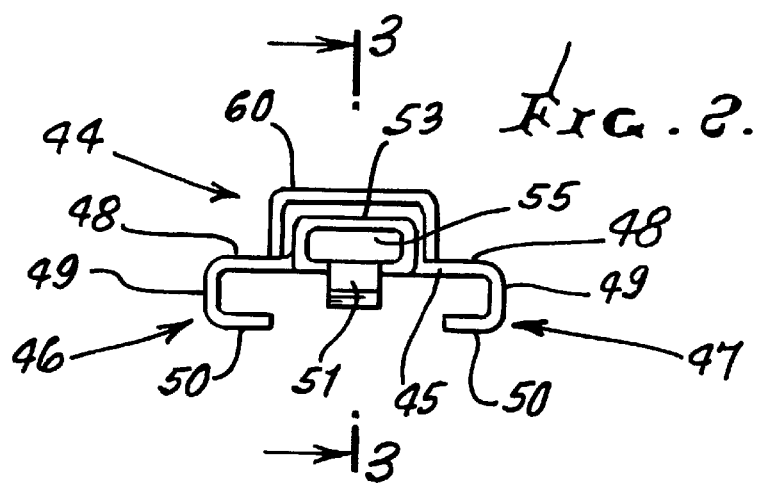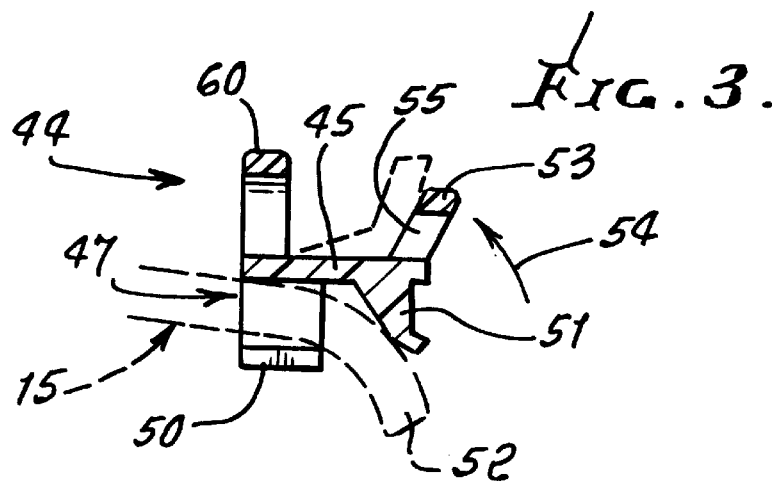

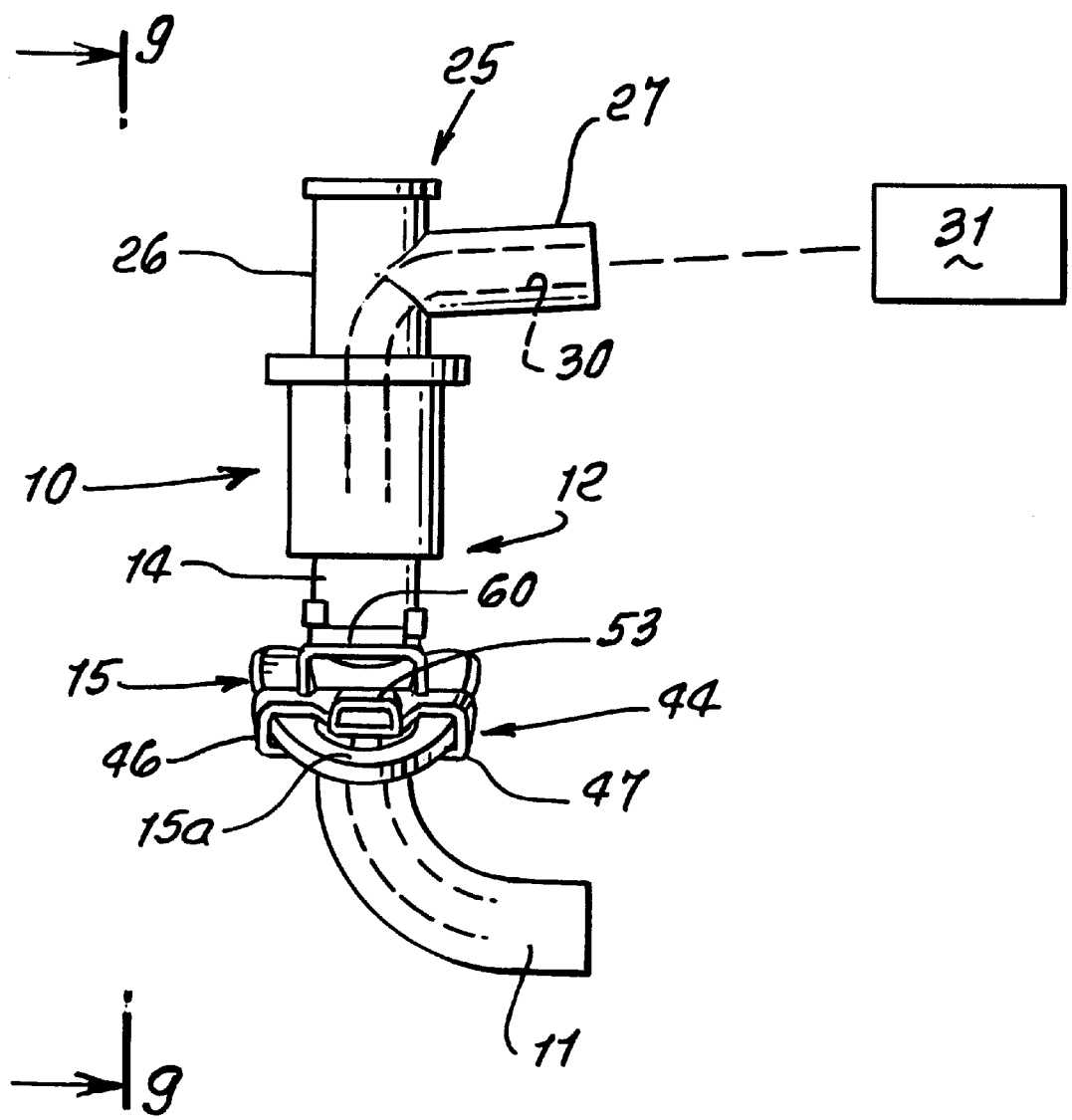

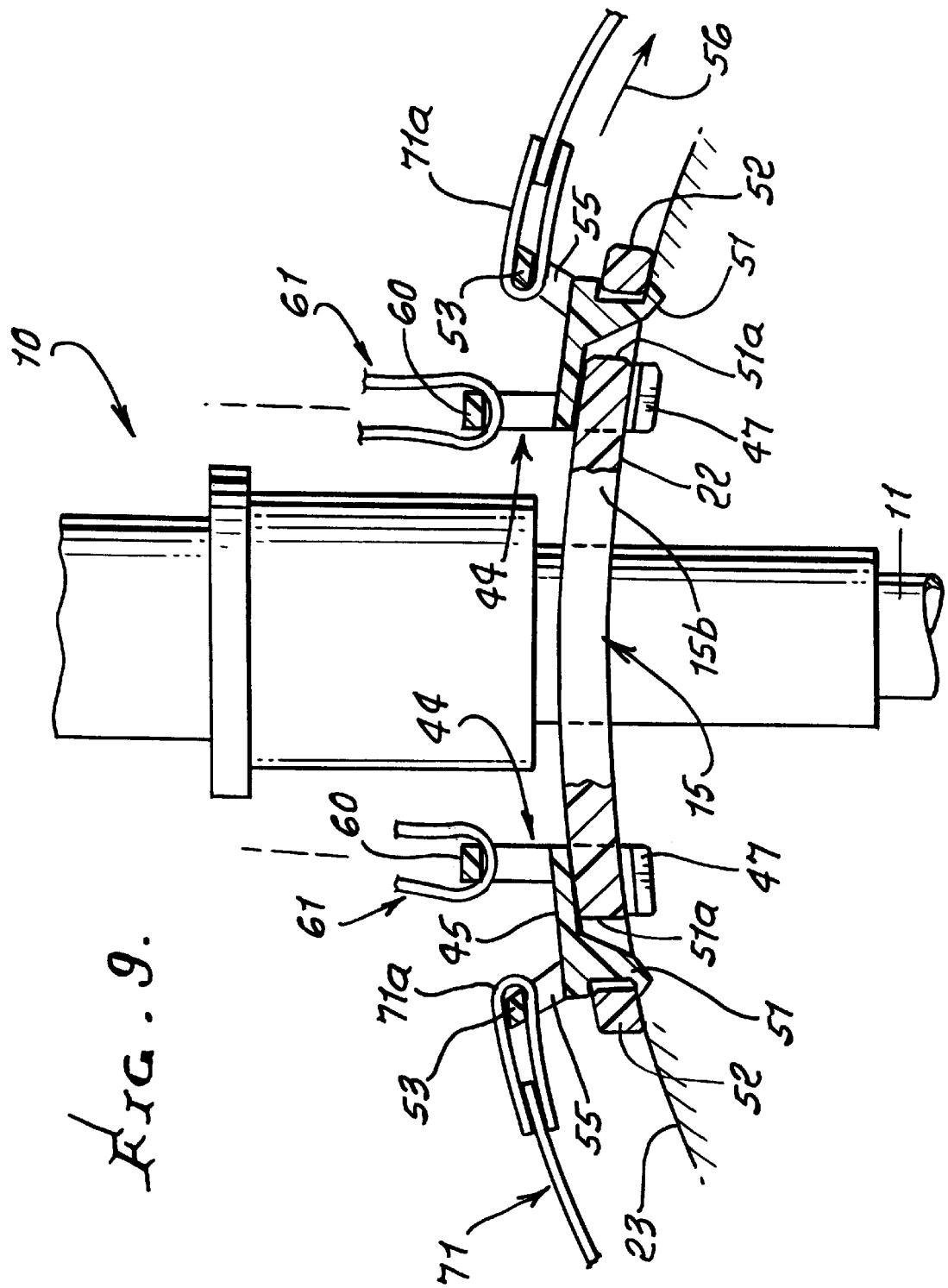

5,975,080

RETENTION SYSTEM FOR ANTI-DISCONNECT APPARATUS AND METHOD, FOR BREATHING SYSTEMS

BACKGROUND OF THE INVENTION

This invention relates generally to use of tracheostomy tubes and associated equipment, and more particularly is addressed to the problem of inadvertent disconnection of elements of such equipment, which can lead to unwanted interruption of breathing.

This invention improves upon the highly advantageous apparatus and method disclosed in U.S. Pat. No. 5,282,463 to Hammersley, and incorporated herein by reference.

Tracheostomy plates have been commonly metallic. Clips were used on such plates to anchor the tracheostomy tie band (i.e., "ties"). Older type tracheostomy ties consisted of twill tape that was clumsily tied to each side of the tracheostomy plate, wrapped around the patient's neck, then tied together on the side of the patient's neck.

Later, with the advent of VELCRO™, tracheostomy ties became a little easier to use. Today, tracheostomy ties consist a variety of materials, such as foam padding, elastic cloth, and wide and narrow materials, to enhance patient comfort. However, all of the tracheostomy ties mentioned above utilize the technique of feeding the tracheostomy tie through the eyelet provided on the tracheostomy tube plate, then fastening in some manner by either tying or using VELCRO™ material.

When the caregiver applies a tracheostomy tie in the conventional manner, the tracheostomy tie is applied under the plate. Some caregivers utilize hemostats or needle holders to attempt to pull the tracheostomy tie through the tie opening, occasionally pinching the patient's skin rather than grabbing the tie. Both of these methods can cause significant discomfort to the patient, while the tracheostomy tube is being manipulated.

The other negative is the time factor. Especially in the current health care market, time is of the essence. If time can be saved in the application of a tracheostomy tie, it would be welcomed.

SUMMARY OF THE INVENTION

This invention relates generally to the use of tracheostomy tubes and associated equipment; more particularly, it addresses the problem of securing a tracheostomy tube onto a patient's neck and additionally securing the ventilator breathing circuit onto the tracheostomy plate.

It is a major object of the invention to provide method and means for preventing inadvertent disconnection of breathing system tubing from associated tracheostomy tubes. Basically, use is made of a neck plate usually carried by the tracheostomy tube and a connector frictionally and telescopically connectible to the tube, as will be seen. In this environment, the basic combination of the invention includes retention apparatus for connecting flexible band means to a tracheostomy neck plate, the neck plate having a wing projecting laterally, the retention apparatus comprising:

a) clip means configured to embrace the wing as the clip means is displaced relative to the wing, the band means attached to the clip means, b) and a detent connection element positioned on the clip to releasably connect to the wing in response to the relative displacing of the clip to embrace the wing.

Another object includes provision of the clip means to have guide means thereon to guide the relative displacement to releasably connect the clip to the wing at a predetermined connection locus, the wing tapering to interfit clip leg means when the detent connects to the wing. That locus is typically defined by shoulders on the clip means and wing that interengage in response to the lateral displacement of the clip means relative to the wing.

Yet another object is to provide a shoulder-defining tang projecting toward and into an opening defined by the wing. In this regard, the wing defined by the plate typically forms the opening extending in or through the wing, allowing easy push out removal of the tang upon resilient bending up of the wing, for releasing the clip from the wing and plate. The latter may consist of resiliently bendable plastic material.

A further object includes provision of a tracheostomy tube retention band means, and anchoring the retention band to the clip. A retention band grip may be provided at the clip for anchoring the retention band to the clip, instead of to the plate, for ease of application.

Dual such slots may be provided in respective association with the first wing, and also with a second wing defined by the plate, for anchoring the retention band to the clip at dual grip locations, there being a tracheostomy tube carried by the plate and located between the grips, and including auxiliary dual grips on the respective clip for anchoring neck band means. The auxiliary grip is angled relative to the tang on the clip to provide a lever for bending the clip to enable tang removal from the opening, for clip release.

These and other objects and advantages of the invention, as well as the details of an illustrative embodiment, will be more fully understood from the following specification and drawings, in which:

DRAWING DESCRIPTION

FIG. 1 is a top plan view of a clip;

FIG. 2 is a front elevation view taken on lines 2—2 of FIG. 1;

FIG. 3 is a section taken on lines 3—3 of FIG. 2;

FIG. 8 is a side elevational view taken on lines 8—8 of FIG. 5; and

FIG. 9 is a front elevational view taken on lines 9—9 of FIG. 8.

DETAILED DESCRIPTION

Figure 4:
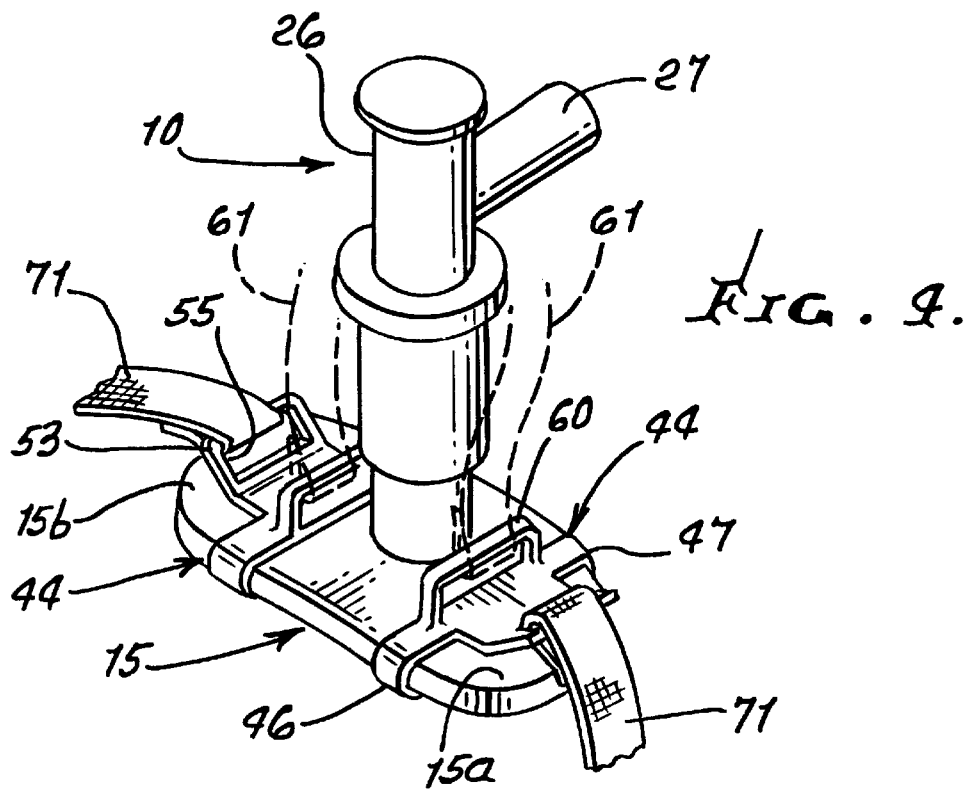
FIG. 4 is a perspective view showing clip attachment to a tracheostomy plate.
Figure 5:
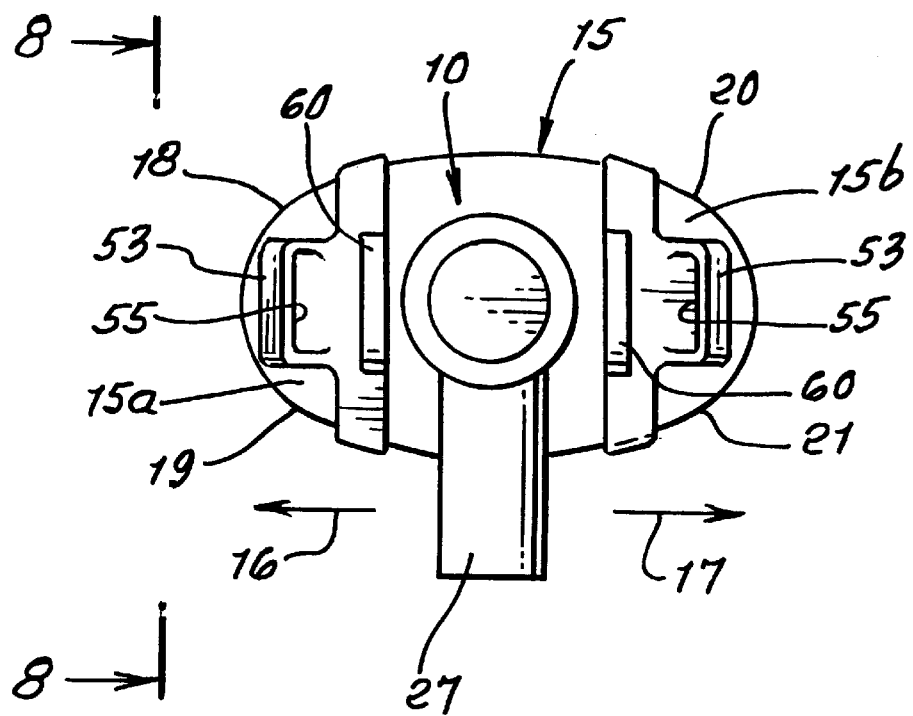
FIG. 5 is a top plan view showing two clips attached to the plate.
Figure 6:
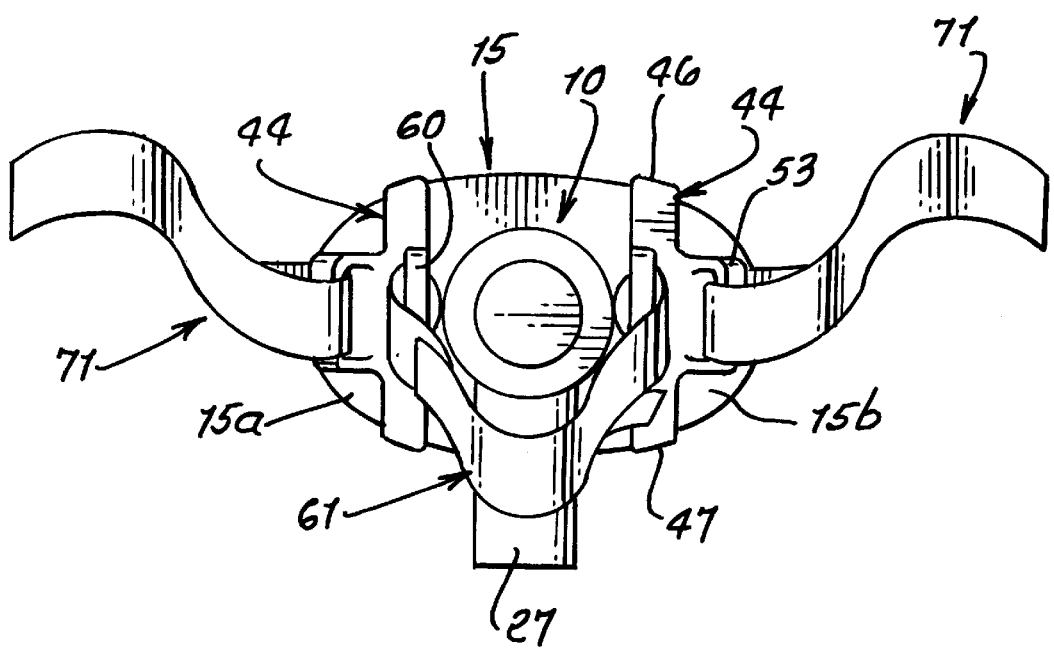
FIG. 6 is a view like FIG. 5, and also showing retention band means attached to the two clips.

In FIGS. 6, 8, and 9, a tracheostomy tube assembly 10 includes an elongated, curved, outer tube section 11 terminating at an enlarged, tubular head section 12. The assembly 10 also commonly includes an inner tube 14 communicating with section 12. A neck plate 15 is carried by section 12, to extend at opposite sides thereof. The plate has wings 15a and 15b which project oppositely, and which narrow in width, in opposite directions 16 and 17. The plate may be oval-shaped as shown.

Wing edges appear at 18–21. Edges 18 and 19 taper in direction 16; and edges 20 and 21 taper in direction 17. The plate also has a face 22 with curvature to fit on a patient's neck 23, when tube section 11 is received through a neck opening and into the trachea. Various other forms of neck plates may be used. A duct, such as an elbow or bend 25, has legs 26 and 27. The elbow leg 27 has a bore 30 to pass air from a breathing system 31 to the tube 11.

In accordance with the invention, improved apparatus is provided to connect a flexible band means to the tracheostomy plate. The band means appears at 71 in FIG. 9 and has opposite end loops 71a. The apparatus comprises:

a) clip means configured to embrace the wing as the clip means is displaced relative to the wing, the band means attached to the clip means, b) and a detent connection element positioned on the clip to releasably connect to the wing in response to the relative displacing of the clip to embrace the wing.

Figure 7:
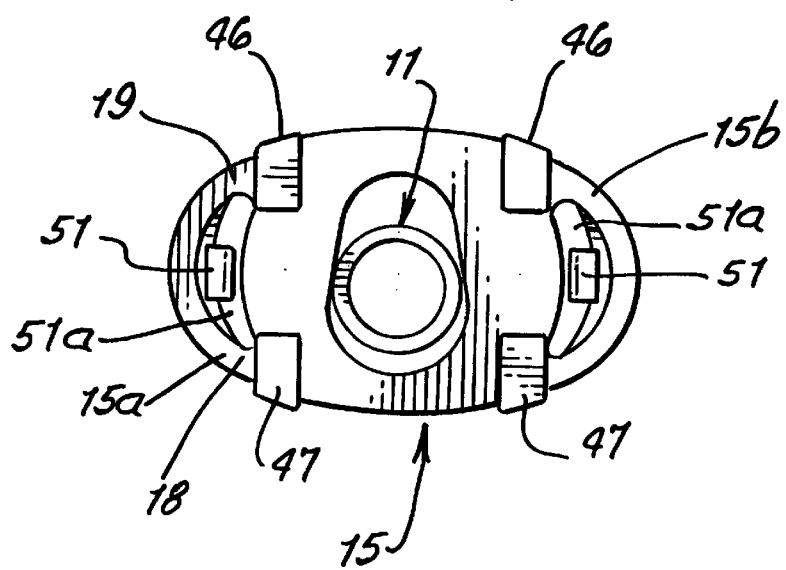
FIG. 7 is a bottom plan view showing legs of the two clips attached to the plate, and retention projections on the clips received in openings formed in the plate.

Referring to FIGS. 1–3, the plastic clip 44 includes a base section 45, and two legs 46 and 47. Each leg has an upper portion 48 integrally connected with the base section to slide along the top of the wing of plate 15, an outer portion 49, and a lower lip portion 50 slidable along the underside of the wing of plate 15. See also FIG. 7. Note that when the clip is fully laterally received on a plate wing, the leg outer portions 49 engage the wing edges 18 and 19, as seen in FIG. 7. At that time, a detent projection in the form of a tang or post 51 is received downwardly into an opening 51a in the wing.

During slide reception of the clip on the wing, the outer, narrow, terminal portion 52 of the wing is resiliently bendable downwardly by the post, by sliding camming action, so that the post rides over terminal portion 52. When the post drops down into the opening, the legs come into close-fitting engagement with the wing edges 18 and 19, as shown in FIG. 7, providing a sturdy, safe and stable locking condition of the clip on the wing. Legs 46 and 47 engage the wing to hold the post in the opening.

In addition, the clip may be easily released from the wing as by pushing upwardly the upwardly angled rightwardly projecting section 53 of the clip (see arrow 54 in FIG. 3), to disengage the tang or post 51 from the opening 51a, followed by rightward slidable removal of the clip off the wing. Bending of base section 45 accommodates this section 53 upward movement.

Section 53 of the clip has the further function of providing an upward looping grip 55, for attachment of the band 71, as seen in FIG. 9. Attachment of the band to the wearer's neck serves to produce force in the arrow direction 56, which in turn has a component urging the grip 55 downwardly toward the plate, thereby retaining the post 51 in the retention opening 51a. Grip 55 therefore serves as a lever having multiple functions.

Also provided on each clip is a grip 60 that projects upwardly relative to base section 45 for retention of the tracheostomy tube retention band means 61, as best seen in FIG. 9. Grip 60 is located directly above the section 45 on which legs 46 and 47 and post 51 are carried, whereby upward force exerted by the band means 61 does not rock the clip to disengage post 51 from the opening.

Grips 55 and 60 are spaced above the level of clip base section 45, whereby attachment of the bands to the grips does not require dislodgment of the clip from the tracheostomy plate.

The method of the invention basically comprises:

a) providing clip means configured to embrace the wing, the band means attached to the clip means, b) displacing the clip laterally relative to the wing, to embrace the wing, c) and providing a detent connection on at least one of the clip and wing to releasably interconnect the clip and wing in response to the relative displacing of the clip to embrace the wing.

I claim:

1. The method of connecting flexible first band means to a tracheostomy neck plate, said neck plate having a first wing projecting laterally, the method including:

a) providing first clip means configured to embrace said wing, the band means attachable to the clip means, b) and providing a detent connection on at least one of the clip means and wing to releasably and positively interconnect and hold the clip means to the wing in spaced relation to the edges of the wing in response to relative displacing of the clip means to embrace the wing, c) said detent connection comprising a tang on the clip means to project toward and come into registration with an opening defined by the wing, and to be received into said opening.

2. The method of claim 1 including providing guide leg means on the clip means to engage the wing and guide said relative displacement to releasably connect the clip means to the wing at a predetermined connection locus, the wing tapering to interfit the leg means when the detent connection interconnects the clip means and wing.

3. The method of claim 1 including providing shoulders on the clip means and wing that interengage in response to said displacement of the clip means relative to the wing.

4. The method of claim 1 including providing legs on the clip means to slidably embrace edges defined by the wing, in response to said displacing of the clip means relative to the wing, for holding said tang in said opening.

5. The method of claim 4 wherein said tang is located between said clip means legs, and is spaced from said legs, and said tang has a cam surface angled relative to the plate to have camming engagement with the wing.

6. The method of claim 5 including providing said plate to consist of resiliently bendable plastic material, whereby bending of said wing allows removal of said tang from said opening.

7. The method of claim 1 including providing a tracheostomy breathing apparatus retention band means, and anchoring said retention band means to said clip means.

8. The method of claim 7 including providing a retention band grip projecting upwardly on the clip means for anchoring the retention band means to the clip means.

9. The method of claim 7 including providing a second clip means like the first clip means and retention band passing dual grips projecting upwardly on the clip means in respective association with said first wing and also with a second wing defined by the plate, for anchoring the retention band means to the clip means at dual locations, there being a tracheostomy tube carried by the plate and located between said grips, and including auxiliary dual grips on the respective clip means for anchoring neck band means, said auxiliary grips projecting relative to said tangs on the clip means to provide levers for bending the clips to enable tang release from the openings in the clip means.

10. A retention system for a tracheostomy neck plate, comprising a) a neck plate having two wings, b) flexible band means, c) first and second clip means configured to embrace said respective wings as the clip means are displaced relative to said wings, the band means attached to said first and second clip means, d) and detent connection elements positioned on the first and second clip means to releasably connect to the wings in response to said relative displacing of the clip means to embrace the wings, e) each detent connection element comprising a tang to project toward and come into registration with an opening defined by a wing, and to be received into said opening f) said tangs being integral with the first and second clip means.

11. The combination of claim 10 wherein each clip means has guide leg means thereon to engage the wing and guide said relative displacement to releasably connect the clip means to the wing at a predetermined connection locus, the wing tapering to interfit the leg means when the detent connection connects to the wing.

12. The combination of claim 11 wherein said predetermined connection locus is defined by shoulders on the clip means and wing that interengage in response to said lateral displacement of the clip means relative to the wing.

13. The combination of claim 10 wherein each said tang has a camming surface angled relative to the plate to cam against and deflect the plate.

* * * * *